United States Patent [19]
Anspach, Jr. et al.

[11] Patent Number: 5,501,695
[45] Date of Patent: Mar. 26, 1996

[54] FASTENER FOR ATTACHING OBJECTS TO BONES

[75] Inventors: William E. Anspach, Jr., Palm Beach Gardens, Fla.; William S. Reid, Knoxville, Tenn.; Eddy H. Del Rio, Royal Palm Beach; William E. Anspach, III, Palm Beach Gardens, both of Fla.

[73] Assignee: The Anspach Effort, Inc.

[21] Appl. No.: 215,279

[22] Filed: Mar. 21, 1994

Related U.S. Application Data

[63] Continuation-in-part of Ser. No. 889,477, May 27, 1992, Pat. No. 5,326,205.

[51] Int. Cl.⁶ .................................................. A61B 17/04
[52] U.S. Cl. .................... 606/232; 606/72; 606/74; 606/75; 411/34; 411/38; 411/43; 411/59
[58] Field of Search ........................ 606/232, 72, 74, 606/75; 411/34, 36–38, 43, 59–61

[56] References Cited

U.S. PATENT DOCUMENTS

| | | | |
|---|---|---|---|
| 3,143,916 | 8/1964 | Rice | 411/37 |
| 3,779,239 | 12/1973 | Fisher et al. | 411/38 |
| 3,896,504 | 7/1975 | Fisher | 411/38 |
| 4,580,936 | 4/1986 | Francis et al. | 411/43 X |
| 4,859,128 | 8/1989 | Brecz et al. | 411/43 |
| 4,877,362 | 10/1989 | Berecz et al. | 411/3 X |
| 5,030,050 | 7/1991 | Auriol et al. | 411/43 X |

*Primary Examiner*—Gary Jackson
*Attorney, Agent, or Firm*—Quarles & Brady

[57] ABSTRACT

A fastener adapted to expand into bone has a tubular body having a longitudinal opening therethrough with a stop within the opening. The body has a head at one end and a longitudinal slot extends through the body near the other end to form ribs that expand radially when the body is compressed. A puller projects through the opening in the rivet and has a head that engages the other end to compress the rivet when the puller is pulled through the body. An annular recess is formed in the puller near the head and the other end of the body is crimped into the recess to aid expansion of the ribs. The puller is weakened at a point so that it will break upon continued pulling after the ribs reach a fully expanded state.

29 Claims, 6 Drawing Sheets

FASTENER FOR ATTACHING OBJECTS TO BONES

This is a continuation-in-part of U.S. patent application Ser. No. 07/889,477 filed on May 27, 1992, now U.S. Pat. No. 5,326,205.

TECHNICAL FIELD

The invention relates to a device for attaching metallic or synthetic plates and sutures to a bone during a surgery.

BACKGROUND OF THE INVENTION

The most common fastener used in the reconstruction of bone fracture fragments in the human body is a screw. Screws of various types are used to directly hold bone fragments together, hold plates onto bone, and to act as anchors for the attachment of tendons and grafts of various types. Screws have certain disadvantages. In soft bone, they gain little purchase; in extremely thin bone, such as about the face, few threads gain purchase for adequate fixation. With the advent of extremely small bone plates for fracture and reconstructive surgical procedures, the screws are so small that just handling them and keeping them on a screwdriver can be difficult. Screws also require a significant amount of time to insert, especially if the hole has to be threaded first.

Various types of "blind" rivets are commonly used in industry. Most of them consist of two parts: a puller and the rivet body. The puller causes a deformation of the rivet body as it is moved in a linear direction. The expansion deformity of the rivet body continues until the expanded area reaches either the rivet head or the material into which the rivet is placed. These types of fasteners work well in sheet metal as the material has sufficient strength to resist further deformation of the rivet body and right fixation, as well as breakaway of the puller shaft is accomplished quite easily. Unfortunately, these designs do not work well in the human body, as bone is not strong enough to stop the progression of the widened rivet body before it contacts the rivet head.

The following patents relate to this subject matter: U.S. Pat. Nos. 1,105,105; 2,494,229; and 4,590,928.

SUMMARY OF THE INVENTION

The object of the present invention is to create a rivet fastener which will be effective for attachment in different types of bone and which will contribute significantly to the ease and rapidity of the fastening procedure.

The rivet is designed to expand into even hard bone to secure the rivet. To gain maximum expansion, the rivet body is slotted longitudinally with the bottom portion tapered so that when it is forced to expand by a puller head, the body forms radial wings, or arms, which extend into both hard and soft bone. The wings, or arms, are created at a distance below the surface of the bone as determined by a tapered-in portion in the rivet body. In one embodiment of the rivet, the slots are angled slightly transverse to the body's longitudinal axis to produce twisted wings with inclined surfaces. Complete deformation of the rivet body to the rivet head is prevented by a puller head stop. The design creates a "blind" rivet which is extremely effective for attaching objects to bone.

Another object of the present invention is to provide a device for attaching sutures to a bone. This can be used for transplantation of tendons, re-attachment of muscles, and basically any needed fixation to bone.

A further object of the invention is to provide a device for directly attaching a torn tendon to a bone without requiring sutures.

DETAILED DESCRIPTION OF THE INVENTION

Figure 1:
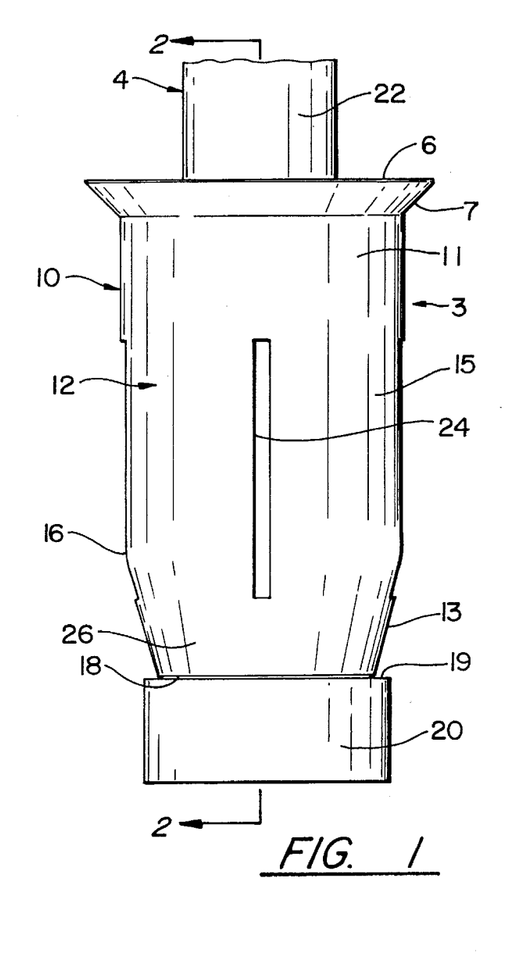
FIG. 1 is a side view of the rivet with the puller in place prior to insertion in a bone.
Figure 2:
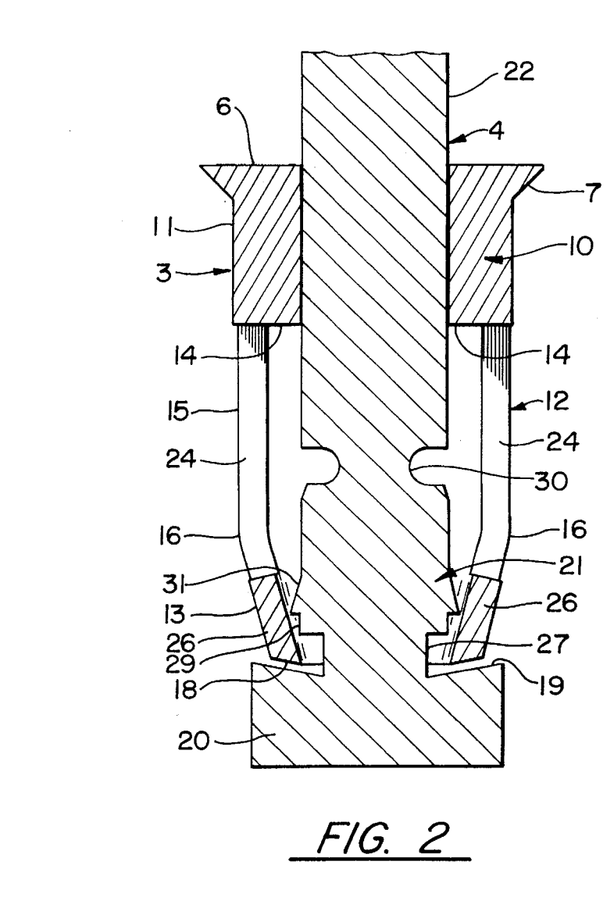
FIG. 2 is a cross-sectional view of the rivet taken along the line 2—2 of FIG. 1.
Figure 3:
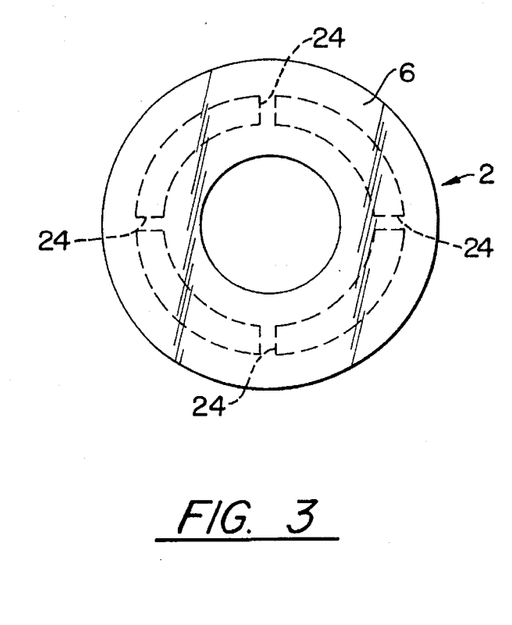
FIG. 3 is a top view of FIG. 1.

Referring to FIGS. 1, 2 and 3, a rivet 3 has an upper annular portion 10 with an annular flange 6 extending radially outward from around the top of the upper annular portion 10. A tapered surface 7 extends from the outer edge of the annular flange 6 downward and inward to the outer surface 11 of the upper annular portion 10 to limit penetration of the rivet into a hole.

The tubular rivet 3 has a lower annular portion 12 extending downward from the bottom of the upper annular portion 10. Lower annular portion 12 has its outer surface 13 formed as an extension of outer surface 11 of upper annular portion 10. The thickness of the lower annular portion 12 is smaller than the thickness of the upper annular portion 10 forming an annular step, or stop, 14, for a purpose to be hereinafter described.

The lower section of the lower annular portion 12 is bent inward at a circumferential bend line 16 and extends to end surface 18 at which an opening is formed at the bottom of the lower annular portion 12. The opening has an inner diameter which is approximately equal to the inner diameter of the upper annular portion 10. A plurality of longitudinal slots 24 is formed in the lower annular portion 12 to below the circumferential bend line 16 at which the lower annular portion tapers inward leaving a solid tapered portion 26 at the lower end 18. Lengthwise ribs 15 are created between the slots 24. The solid tapered portion 26 terminates at end surface 18 which is beveled at approximately eight degrees to aid in bending the rivet 3 during fastening, as will be described.

A puller 4 has a head 20, an intermediate section 21 and a puller rod 22. The puller rod 22 extends upward through the inner diameter of the lower part of the rivet's annular portion 12 and the inner diameter of the rivet's upper annular portion 10. The puller rod 22 is undercut at point 30 to provide a weakened section at which the puller rod will break upon the intermediate section engaging the step, or stop, 14 when the rivet 3 has been fixed in place. The contoured intermediate section 21 between the head 20 and puller rod 22 aids in securing the rivet 3. This section 21 has an annular, cylindrical recess 27 adjacent head 20, then a shoulder 29 going up the puller and then a flared region 31 contiguous with rod 22. As will be described, the recess forms a rectilinear, annular groove into which the end of the lower portion 12 of the rivet 3 slides during fastening. During fabrication, the tapered portion 26 at the lower end of the rivet 3 is crimped into the puller recess 27. This crimping not only captures the rivet on the puller to hold those components together, the crimping also defines the subsequent bending action which fastens the rivet in a hole.

The cylindrical head 20 is integral with the lower end of the puller 4 and is larger than the opening in end surface 18 of the rivet. The top surface 19 of the head 20 faces the beveled end surface 18. Although the top surface 19 can be flat, preferably that surface tapers toward the exposed end of the head going inward toward the center of the puller 4. The angle of incline of the top surface 19 of the head is substantially the same and the angle of incline of the beveled end surface 18 of the rivet 3. The beveled surfaces direct the lower end of the rivet inward during fastening.

Figure 4:
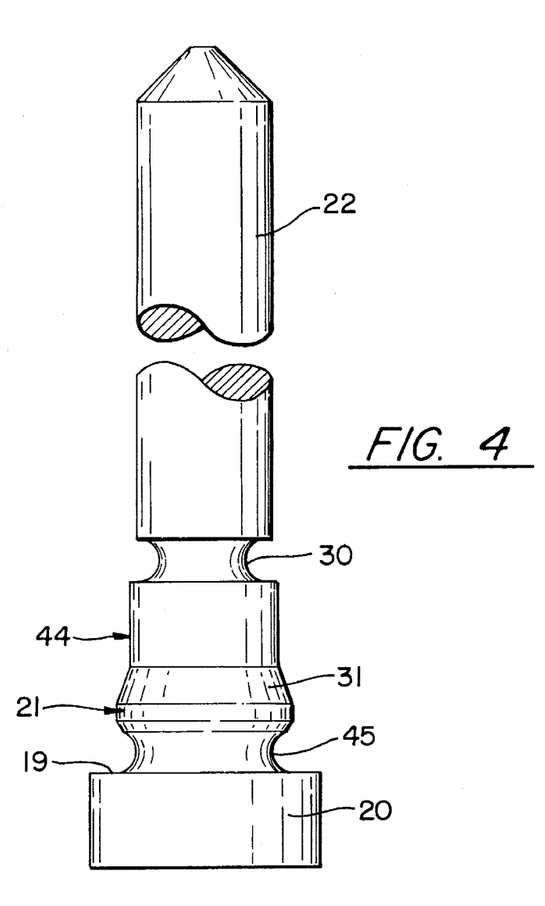
FIG. 4 illustrates a second embodiment of the puller.

FIG. 4 shows another version of a puller 44 that can be used with the rivet 3. This version has a curved recess 45 to receive the end of the rivet 3. The surface 19 of the puller head 20 still is tapered inward as in puller 4.

The two-part bone rivet assembly, the rivet 3 and puller 4 or 44, is formed of a biologically compatible material. For example, the rivet 3 is machined from a cylinder of titanium, and the puller 4 or 44 is formed of cold forged titanium. The outer diameter of the puller rod 22 and the inner diameter of the end of the rivet 3 are sized for an interference fit so that the rivet 3 and puller member 4 remain as one unit, or assembly, before use.

Figure 5:
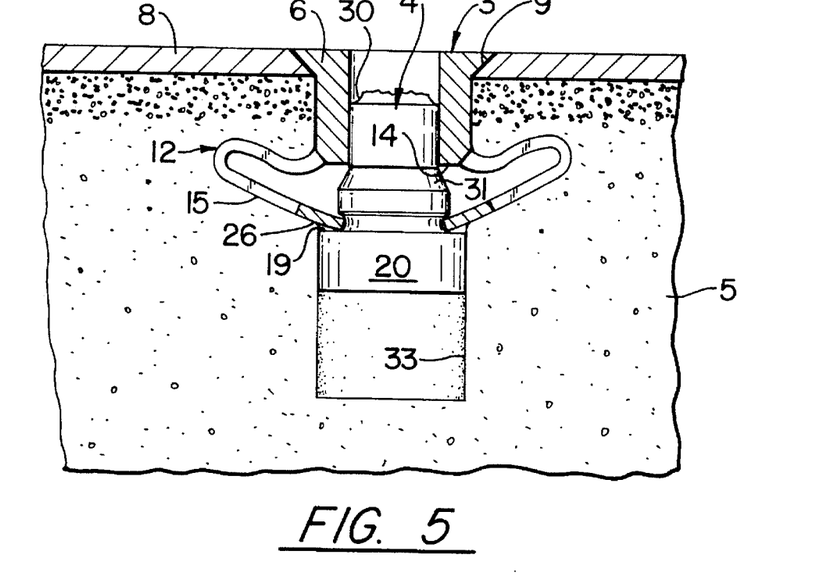
FIG. 5 is a sectional view of a rivet fastened in a hole in relatively soft bone.
Figure 6:
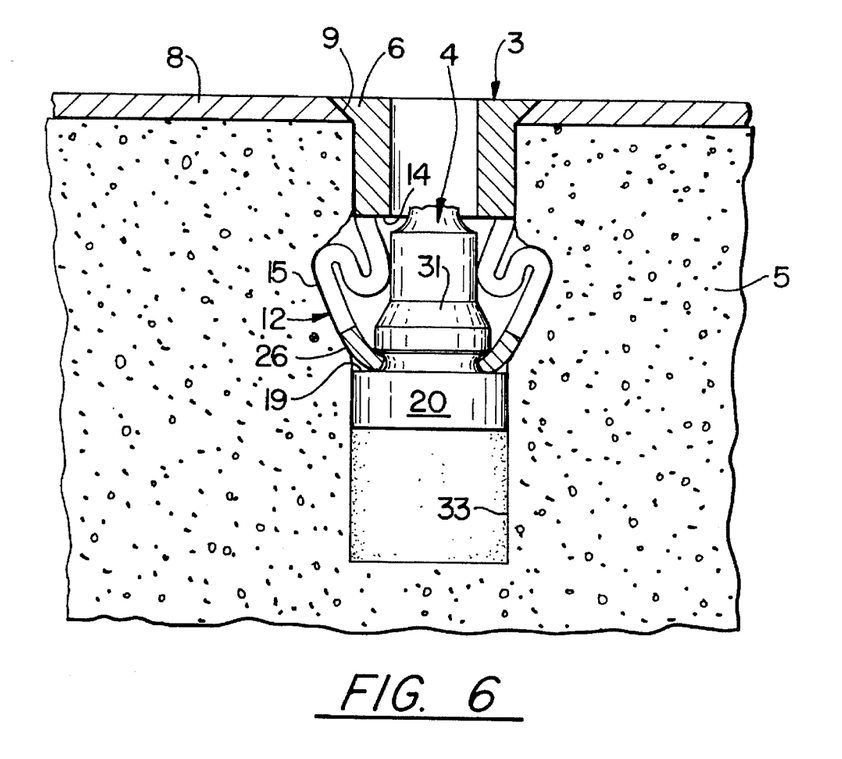
FIG. 6 is a sectional view of a rivet fastened in relatively hard bone.

With reference to FIGS. 5 and 6, the rivet 3 can be used to attach a plate 8 to a bone 5. The plate 8 has a hole 9 with tapered walls that match the tapered surface 7 of the rivet. The rivet extends through the plate and into a hole 33 that was drilled into the bone 5. Once the rivet 3 is in place, a surgical instrument is attached to the free end of the puller rod 22 and placed against the rivet end flange 6. The instrument then pulls the puller rod 22 upward causing the head 20 of the puller 4 to react with the lower portion 12 of the rivet 3. The reaction of the inwardly tapered top surface 19 of the puller head 20 against the beveled lower end surface 18 of the rivet directs and guides the lower end of the rivet inward while longitudinally compressing the rivet. The longitudinal compression deforms the lengthwise ribs 15 expanding them radially outward with the deformation depending on the particular structure of the bone 5.

In FIG. 5, the rivet 3 is placed in "soft" bone, where the lengthwise ribs 15 of the lower annular portion 12 have been forced radially upward and outward, bending into a U-shape that extends into the bone 5. It can be seen that the plurality of slots 24 will permit a plurality of ribs 15 to extend outward as arms.

In FIG. 6, the rivet 3 is placed in "hard" bone where the lengthwise ribs 15 of the lower annular portion 12 do not extend as far the ribs extend into softer bone. In this case, the ribs 15 are compressed into an S-bend by the wall of the hole in the hard bone 5. The top surface 19 of the puller head 20 also forces the solid tapered portion 26 outward driving that portion into the bone 5.

While "hard" and "soft" bones 5 have been discussed as examples, it is to be understood that the hardness of a bone can fall anywhere in the range between a "hard" bone which permits only limited radial expansion of the rivet ribs 15 into the bone 5, and a "soft" bone which permits the ribs 15 to extend fully into the bone. However, regardless of the bone hardness, the rivet 3 expands to become embedded in the bone thereby providing more than mere friction engagement with the bone.

The location of the expanded portion of the rivet 3 below the surface of the bone 3 is determined by the length of the upper annular portion 10. It is desirable that the upper annular portion 10 of the rivet 3 be of such a length that the top of the "holding" expansion of the rivet 3 is formed below the surface of the bone to obtain the proper holding location. This length places the annular stop 14 below the surface layer of the bone to form the top of the "holding" expansion. The length of the upper annular portion 10 can vary with longer portions than the one shown in the drawings being useful to graft together two fragments of bone. In addition, the length of the lower annular portion 12 can vary to provide ribs of different lengths that expand by varying amounts into the bone.

As the puller 4 is drawn upward out of the rivet 3, the flared region 31 strikes the step, or stop, 14 at the lower end of the upper portion 10 of the rivet as shown in FIG. 5. Application of additional force to extract the puller 4 from the rivet 3 causes the puller to break at the undercut 30. In hard bone as shown in FIG. 6, the resistance to expansion of the rivet is so great that the rod 22 breaks at undercut 30 before the flared region 31 strikes the step, or stop, 14 on the rivet.

It can be seen that the puller head 20, in the position at which the rod 22 breaks will hold the ribs 15 outward in their expanded position, as shown in FIGS. 5 and 6. This is also true of intermediate positions. This positioning of puller head 20 aids in preventing withdrawal of the rivet 3 from the hole.

Figure 7:
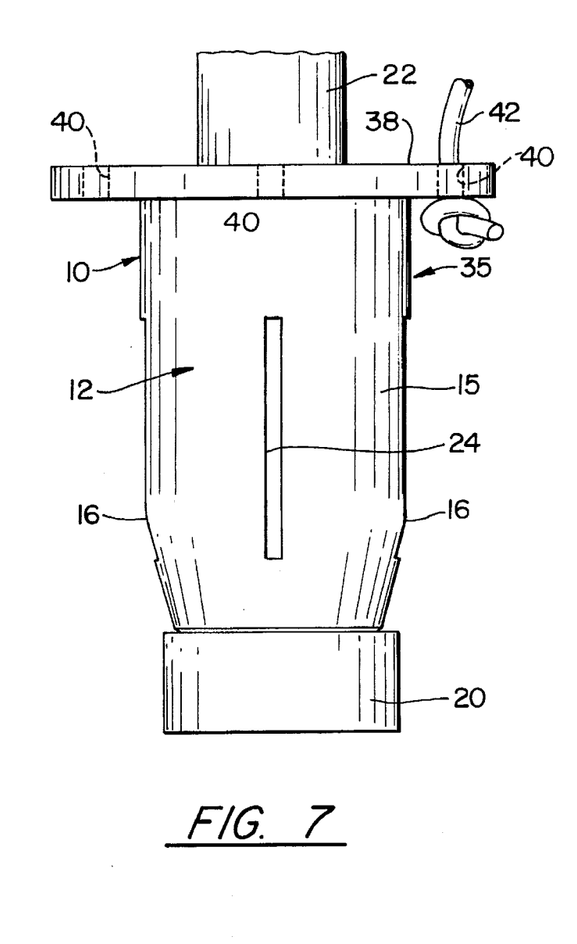
FIGS. 7 and 8 side and top views respectively of a modified rivet for attaching a suture.
Figure 8:
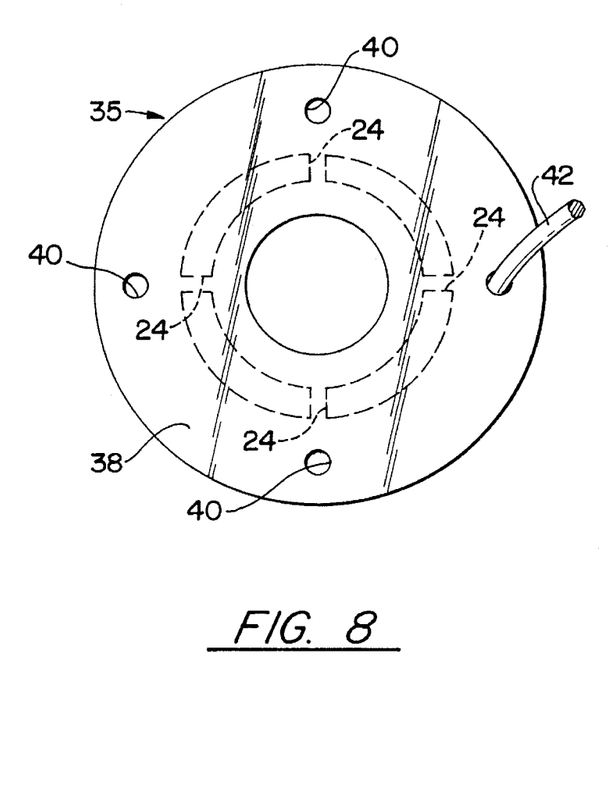

FIGS. 7 and 8 show a bone rivet device with a rivet 35 having an integral disk-like flange 38 with four holes 40 around the top at which to affix a suture 42. A single suture 42 can be affixed to one hole 40 by being tied as in FIG. 8. A suture 42 can be threaded through two holes 40 from one side making two suture ends available.

Figure 9:
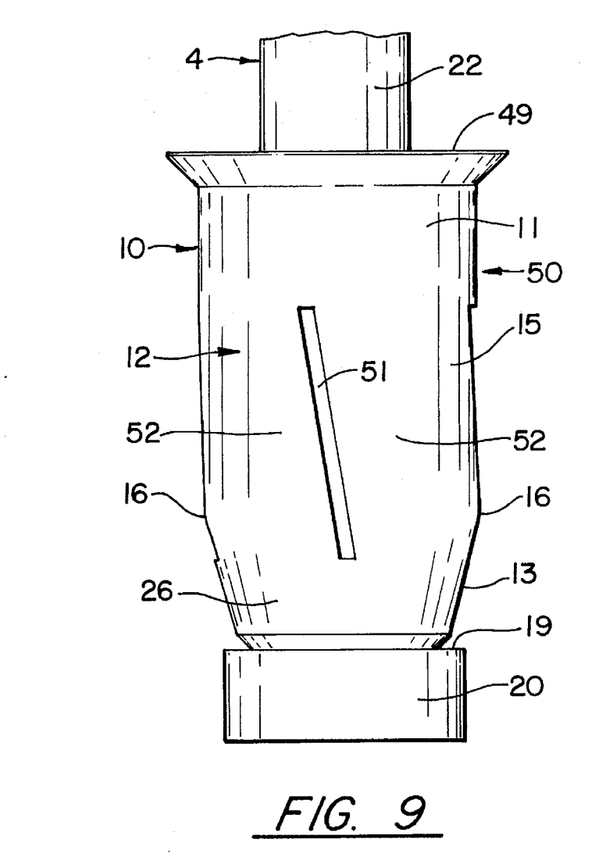
FIG. 9 illustrates a side view of another embodiment of a bone rivet according to the present invention.
Figure 10:
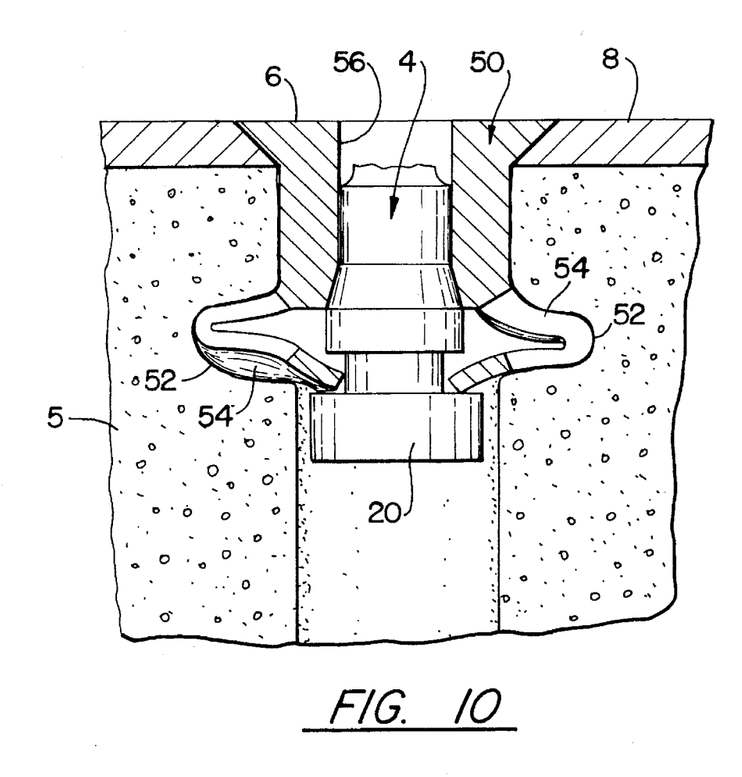
FIG. 10 shows the bone rivet in FIG. 9 fastened in a hole in bone.

In another embodiment shown in FIG. 9, the slots 51 in the lower annular portion 12 of the rivet 50 are formed at an acute angle to the longitudinal axis of the body. Ribs 52 are created between the slots 51. The head 49 of this rivet can be either flared as shown in FIG. 9 or a suture flange 38 as in FIG. 7. When rivet 50 is compressed by the puller 4, the ribs 52 twist as the ribs expand into the bone 5 to form screw-like inclined surfaces 54 as shown in FIG. 10. This rib formation facilitates removal by allowing the rivet 50 to be screwed out of the bone 5. For example, conventional screw extractor can be twisted into the central opening 56 in annular flange 6 and then turned to back rivet 50 out of the hole in the bone.

Figure 11:
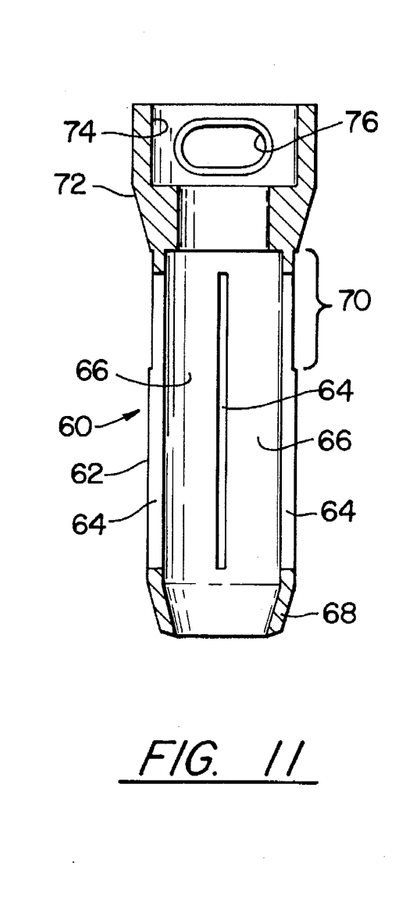
FIG. 11 illustrates yet another embodiment of a bone rivet with potions of the ribs having a reduced thickness to achieve a specific pattern of rib expansion during fastening.
Figure 12:
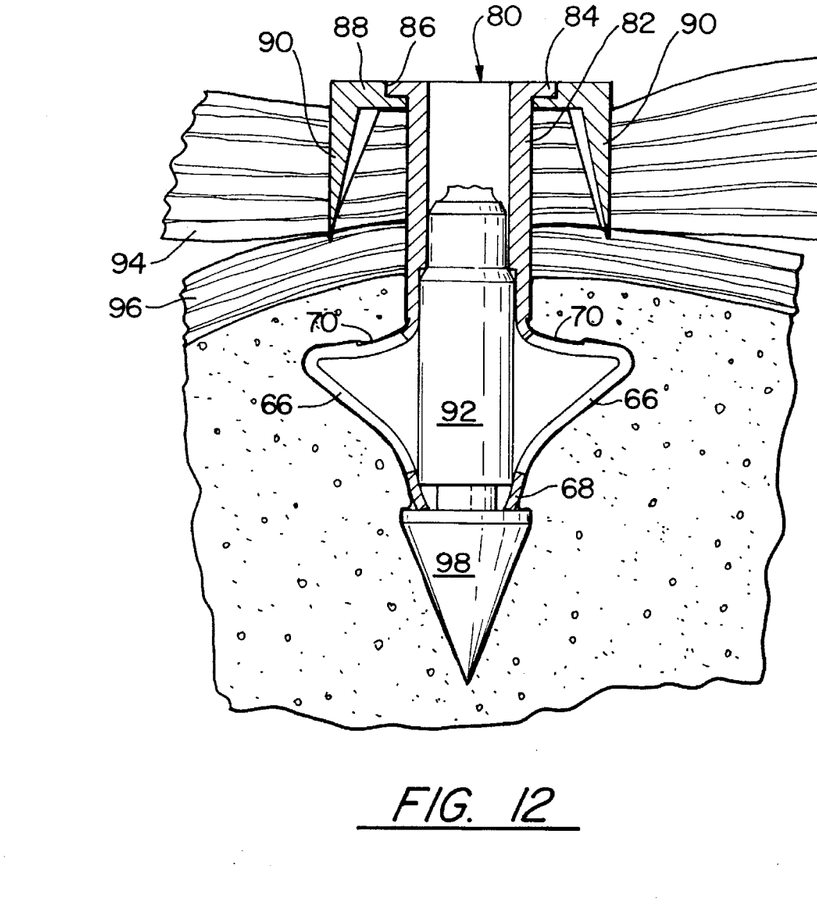
FIG. 12 is a cross-section view of a rivet assembly adapted to attach a torn tendon to a bone.

A different version of a rivet 60 for anchoring sutures is depicted in FIG. 11. This rivet 60 has a tubular body 61 with a plurality of longitudinal slots 64 which define separate ribs 66 between the slots. Lower annular portion 68 of the body 62 is tapered inward to engage the head of a puller (not shown) in a similar manner to the way in which the lower ends of the previously described rivets engage the puller head. The upper one-third portion 70 of each rib 66 is reduced in thickness which results in the ribs bending as shown in FIG. 12. Although that latter Figure illustrates a rivet having a different upper section, the ribs expand or flare outward in the same manner during fastening. Specifically, the upper rib portion 70 of reduced thickness projects a substantially perpendicular to the body of the rivet with the remainder of the rib extending at approximately 45 degrees from the lower annular portion 68.

The upper section 72 of the body of rivet 60 in FIG. 11 has an enlarged inner diameter region 74 with a pair of diametrically opposed slot apertures 76 through the body wall. The apertures receive a pair of sutures (not shown) with each suture extending through and between the slots around a different side of the puller that projects through the rivet. When the rivet 60 is inserted into a hole drilled in bone and the puller is pulled, the upper rivet section 72 is drawn beneath the surface of the bone with the sutures secured between the bone and the rivet. During fastening into bone, the puller will break at a point below the slot apertures 76 and not interfer with the sutures.

FIG. 12 shows a version of a bone rivet 80 for reattaching torn tendons to a bone 96. The ribbed section of the body of rivet 80 is the same as the rib structure of the rivet 60 in FIG. 11. However, the upper section 82 of rivet 80 has an elongated tubular shape and terminates in an outward flange 84. The rivet 80 extends through an aperture 86 in a disk 88 with the outward flange 84 of the rivet fitting into a countersunk region of the aperture. A plurality of pointed barbs 90 are spaced around the perimeter of the disk 88 projecting downward substantially parallel to the longitudinal axis of the rivet. Alternatively, the barbed disk 88 could be an integral part of the rivet 80.

To attach a torn tendon 94 to a bone 96, the assembly of rivet 80, barbed disk 88 and puller 92 are pushed through the tendon. The puller 92 has a pointed tip 94 to aid the assembly piercing through the tendon 94. The barbs 90 also pierce the tendon with sections of the tendon passing between the barbs to secure the tendon to the rivet assembly. The lower portion of the rivet 80 and puller 92 then are inserted into a hole drilled into the bone 96. The puller is drawn through the rivet causing the ribs 66 to expand outward into a relatively soft interior of the bone 96. This action also draws the barbs 90 into the outer surface of the bone 96 thereby securing the tendon, that is captured among the barbs, to the bone.

We claim:

1. A rivet for expanding into a hole in a material, said rivet comprising a tubular body having an exterior surface for fitting into the hole and having a projection extending radially from a first end of the body for controlling an extent to which said rivet can extend into the hole, the body having an aperture extending therethrough from the first end to a second end wherein the aperture has a first diameter in a first portion of the body adjacent to the first end and a second diameter in a second portion of the body adjacent to the second end of the body wherein the first diameter is smaller than the second diameter to thereby form an annular step in the aperture, the exterior surface at the second portion tapers inward toward the second end which has an end surface that is beveled toward the aperture, said body further includes a plurality of elongated slots extending along the exterior surface spaced from both the first end and the second end and communicating with the aperture and said elongated slots defining longitudinal ribs in the body between the slots, wherein the ribs expand radially into the material upon compression of the body.

2. The rivet as recited in claim 1 wherein an end of each of the elongated slots is substantially coplanar with the annular step.

3. The rivet as recited in claim 1 wherein the body includes a solid annular ring at the second end connecting the ribs.

4. The rivet recited in claim 1 wherein a section of each rib has a reduced thickness compared to a remainder of each rib.

5. The rivet as recited in claim 1 wherein the elongated with slots are transverse to a longitudinal axis of the body.

6. The rivet as recited in claim 1 wherein the elongated with slots are angled with respect to a longitudinal axis of the body to twist the ribs as the ribs expand radially during compression of the rivet.

7. The rivet recited in claim 1 wherein the projection has an aperture therethrough to receive a suture.

8. The rivet recited in claim 1 further in combination with a puller comprising a rod and a head wherein the rod extends through the body of the rivet, and the head is connected to the rod for engaging the second end of the rivet to compress the body as the rod is pulled through the body.

9. The rivet as recited in claim 8 wherein the head has an inwardly tapering surface engaging the second end of said rivet.

10. A fastener for expanding into a hole in a material, said fastener comprising:

a rivet having a tubular body with first and second ends, an exterior surface, the body with an aperture extending therethrough from the first end to the second end wherein the aperture has a first cross sectional area in a first portion of the body adjacent to the first end and a second cross sectional area in a second portion of the body adjacent to the second end of the body wherein the first cross sectional area is smaller than the second cross sectional area thereby forming an annular step in the aperture, a plurality of elongated slots extending along the exterior surface spaced from both the first end and the second end and communicating with the aperture and said elongated slots defining longitudinal ribs in the body between the slots which ribs expand into the material when said rivet is compressed, and a puller for compressing the rivet, said puller comprising a rod, a head and an intermediate section connecting the rod to the head, wherein the rod fits within the first portion of the body, the head being incapable of fitting through the aperture at the second end, and the intermediate section fitting within the aperture in the second portion of the body while being incapable of fitting in the aperture in the first portion of the body, the intermediate section forming a recess for capturing the second end of the rivet, said recess being free of restrictions to movement of the second end of the rivet.

11. The fastener as recited in claim 10 wherein the puller is located in the aperture of the rivet with the second end of the rivet being crimped into the recess of the puller.

12. The fastener as recited in claim 10 wherein an end of each of the elongated slots is substantially coplanar with the annular step.

13. The fastener as recited in claim 10 wherein the exterior surface of the second portion tapers inward toward the second end.

14. The fastener as recited in claim 13 wherein an end surface at the second end of said rivet is beveled inward for engaging the head of said puller during rib expansion.

15. The fastener as recited in claim 14 wherein the head of said puller has an inwardly tapering surface for engaging and guiding the second end of said rivet.

16. The fastener as recited in claim 10 wherein said rivet includes a solid annular ring at the second end connecting the ribs.

17. The rivet as recited in claim 10 wherein a section of each rib has a reduced thickness compared to a remainder of each rib.

18. The fastener as recited in claim 10 wherein the elongated with slots are at an acute angle with respect to a longitudinal axis of the body of the rivet.

19. The fastener as recited in claim 10 wherein the elongated with slots are angled with respect to a longitudinal axis of the body to twist the ribs as the ribs expand radially during compression of the rivet.

20. The fastener as recited in claim 10 wherein the rivet has a flange extending outward from the first end of the body with an aperture through the flange for receiving a suture.

21. The fastener as recited in claim 10 wherein the aperture has a third cross sectional area in a third portion of the body between the first end and the first portion of the body wherein the third cross sectional area is greater than the first cross sectional area, and another aperture extends in the third portion from the aperture through the exterior surface for receiving a suture.

22. The fastener as recited in claim 10 wherein the body has an outwardly flared section adjacent to the first end, and another aperture extends in the outwardly flared section from the aperture through the exterior surface for receiving a suture.

23. The fastener as recited in claim 10 further comprising a disk having an aperture with said rivet received therein, and having a plurality of barbs projecting from said disk substantially parallel to a longitudinal axis the body.

24. The fastener as recited in claim 10 wherein the rod of said puller has a weakened point at which the rod will break when pulled further after the intermediate section contacts the annular step.

25. The fastener as recited in claim 10 wherein the second portion of the body is contoured so that the ribs will bend outward when said rivet is compressed by said puller.

26. The fastener as recited in claim 10 wherein the first portion of the body has a predefined length which determines an expansion limit of the rivet.

27. A fastener for expanding into a hole in a material, said fastener comprising:

a rivet having a tubular body with first and second ends, an exterior surface and a projection extending radially from the first end, the body having an aperture extending therethrough from the first end to the second end wherein the aperture has a first diameter in a first portion of the body adjacent to the first end and a second diameter in a second portion of the body adjacent to the second end of the body wherein the first diameter is smaller than the second diameter thereby forming an annular step in the aperture, a plurality of elongated slots extending along the exterior surface spaced from both the first end and the second end and communicating with the aperture in the second portion of the body and said elongated slots defining longitudinal ribs in the body between the apertures, and a puller located in the aperture for expanding said rivet, said puller comprising a rod, a head and an intermediate section connecting the rod to the head, wherein the rod has a diameter that is less than the first diameter, the head has a diameter that is greater than the second diameter and the intermediate section having surface that engages the step to restrict movement of said puller through the aperture in the rivet, the intermediate section forming a recess for capturing the second end of the rivet, said recess being free of restrictions to movement of the second end of the rivet.

28. The fastener as recited in claim 27 wherein the head when positioned against the step prevents the ribs from being forced inward.

29. The rivet as recited in claim 27 wherein a section of each rib has a reduced thickness compared to a remainder of each rib.

* * * * *